United States Patent
Chao

(10) Patent No.: US 7,223,560 B2
(45) Date of Patent: May 29, 2007

(54) NON-LYTIC BACULOVIRUS

(75) Inventor: Yu-Chan Chao, Taipei (TW)

(73) Assignee: Academia Sinica, Taipei (TW)

( * ) Notice: Subject to any disclaimer, the term of this patent is extended or adjusted under 35 U.S.C. 154(b) by 12 days.

(21) Appl. No.: 10/775,050

(22) Filed: Feb. 9, 2004

(65) Prior Publication Data

US 2004/0224410 A1    Nov. 11, 2004

Related U.S. Application Data

(60) Provisional application No. 60/445,951, filed on Feb. 7, 2003.

(51) Int. Cl.
*C12N 15/866* (2006.01)
*C12N 15/63* (2006.01)
*C12P 21/00* (2006.01)
*C12Q 1/68* (2006.01)
*C12Q 1/70* (2006.01)

(52) U.S. Cl. ............... 435/69.1; 435/235.1; 435/320.1

(58) Field of Classification Search ............... None
See application file for complete search history.

(56) References Cited

U.S. PATENT DOCUMENTS

2002/0115157 A1 * 8/2002 Davis et al. ............... 435/69.7
2003/0022377 A1 * 1/2003 Juang et al. ............... 435/456

OTHER PUBLICATIONS

Hughes et al., J. Gen. Virol., 1997, vol. 78, pp. 1801-1805.*
Carbonell et al., J. Virol., 1985, vol. 56, No. 1, pp. 153-160.*
E. De Bernardez Clark. "Refolding of recombinant proteins". Current Opinion in Biotechnology 9:157-163, 1998.
A. A. Deniz et al. "Single-molecule protein-folding: Diffusion fluorescence resonance energy transfer studies of the denaturation of chymotrypsin inhibitor 2". PNAS 97(10):5179-5184, May 9, 2000.
S. Ghaemmaghami et al. "Quantitative protein stability measurement *in vivo*". Nature Structural Biology 8:(10):879-882, Oct. 2001.
J-C Lee et al. "Persistent Baculovirus Infection Results from Deletion of the Apoptoptic Suppressor Gene *p 35*". Journal of Virology 72(11):9157-9165, Nov. 1998.
G. S. Lakshmikanth et al. "Structure is lost incrementally during the infolding of barstar". Nature Structural Biology 8(9):799-804, Sep. 2001.
C. Nishimura et al. "Fluorescence Energy Transfer Indicates Similar Transient and Equilibrium Intermediates in Staphylococcal Nuclease Folding". J. Mol. Biol. 299:1133-1146, 2000.
B. Schuler et al. "Probing the free-energy surface for protein folding with single-molecule fluorescence spectroscopy". Nature 419:743-747, 2002.
Z. Serber et al. "In-Cell NMR Spectroscopy". Biochemistry 40(48):14317-14323, Dec. 4, 2001.

* cited by examiner

*Primary Examiner*—David Guzo
(74) *Attorney, Agent, or Firm*—Fish & Richardson P.C.

(57) ABSTRACT

A baculovirus that infects a host cell without lyzing the host cell and related protein expression method. Within the scope of this invention are in vitro and in vivo methods for detecting protein folding or a cell lysis activity of a sample. Also within the scope of this invention is a method of screening for a compound for treating a disease associated with misfolding of a protein.

5 Claims, No Drawings

SEQUENCE LISTING

<160> NUMBER OF SEQ ID NOS: 3

<210> SEQ ID NO 1
<211> LENGTH: 47
<212> TYPE: DNA
<213> ORGANISM: Artificial Sequence
<220> FEATURE:

-continued

```
<223> OTHER INFORMATION: Primer

<400> SEQUENCE: 1
gaagatcttt ggtccctcgt ggaagcatgg aagacgccaa aaacata                    47

<210> SEQ ID NO 2
<211> LENGTH: 47
<212> TYPE: DNA
<213> ORGANISM: Artificial Sequence
<220> FEATURE:
<223> OTHER INFORMATION: Primer

<400> SEQUENCE: 2
caccggtcca tgatgatgat gatgatgcaa ttccactttc cgccctt                    47

<210> SEQ ID NO 3
<211> LENGTH: 23
<212> TYPE: DNA
<213> ORGANISM: Artificial Sequence
<220> FEATURE:
<223> OTHER INFORMATION: Primer

<400> SEQUENCE: 3
ggggtaccaa tattaacgct tac                                              23
```

NON-LYTIC BACULOVIRUS

RELATED APPLICATION

This application claims priority to U.S. Provisional Application Ser. No. 60/445,951, filed on Feb. 7, 2003, which is incorporated by reference in its entirety.

BACKGROUND

Baculoviruses are a group of rod-shaped, enveloped, double-stranded DNA viruses having a circular, supercoiled genome varying from 90 to 160 kb in size. They have been successfully used for efficient expression of engineered proteins. A baculovirus system is more attractive than other protein expression systems because of its high level expression, posttranslational modification ability, and safety for use in humans (Smith et al., 1983, Mol. Cell Biol. 3, 2156-2165).

However, the conventional baculovirus expression system has one disadvantage. More specifically, host cells infected with baculoviruses lyse upon maturation of viral progenies. During the cell lysis, (1) the engineered protein leaks and is difficult to recover, leading to low protein yields; (2) the host cell lysosomes break down and release proteases, causing degradation of the engineered protein; (3) endoplasmic reticules and Golgi bodies also break down, resulting in poor posttranslational modification and blockade of intracellular trafficking of a membrane or secretory engineered protein. Thus, there is a need for a non-lytic baculovirus.

SUMMARY

This invention is based on an unexpected discovery of a number of non-lytic baculovirus mutants.

Accordingly, one aspect of this invention features a baculovirus that infects host cells, e.g., insect cells, without lyzing them. That is, the majority (i.e., at least 50%) of the host cells infected with the baculovirus are not lyzed upon maturation of viral progenies. In one embodiment, the baculovirus contains an exogenous nucleic acid sequence that encodes a polypeptide. An exogenous nucleic acid sequence refers to any nucleic acid sequence that is not part of the baculovirus genome in nature. One can infect a host cell with such a baculovirus to express the polypeptide. This polypeptide can be a fusion protein that contains a fluorophore. A fluorophore refers to a single fluorescent amino acid residue (e.g., tryptophan, lysine, cystine, or their fluorescent derivatives) or a fluorescence peptide sequences having at least 2 (e.g., 3, 4, 5, 10, 50, and 100) amino acid residues, i.e., fluorophore domain. Examples of a fluorophore domain include enhanced yellow fluorescence protein (EYFP), enhanced cyan fluorescence protein (ECFP), enhanced green fluorescence protein (EGFP), and DsRed. This fluorophore-containing fusion protein can be used to detect protein folding in vitro and in vivo as described below.

Another aspect of the invention features a method for detecting protein folding. The method requires the use of a protein that contains a donor fluorophore domain and an acceptor fluorophore domain, e.g., ECFP and EYFP. The two fluorophore domains are disposed so that, when the protein is folded, they are in close proximity to allow resonance energy transfer between them. The method includes monitoring fluorescence emission change of the acceptor fluorophore domain upon irradiation of the donor fluorophore domain with an excitation light. The change is a function of the protein folding.

The invention also features a method for detecting protein folding in a cell. This method is identical to the method just described, except that it requires the use of a cell expressing a protein that contains a donor fluorophore and an acceptor fluorophore. In one embodiment, these fluorophores are two different fluorescence protein domains, e.g., ECFP and EYFP. The cell is a bacterial, a yeast, an insect, a plant, or a mammalian cell. Preferably, it is an insect cell.

The invention further features a method of screening for a compound for treating a disease associated with misfolding of a protein, such as cystic fibrosis, a disorder associated with misfolded cystic fibrosis transmembrane conductance regulator. The method requires incubating in a first medium a compound and a plurality of cells that have a protein linked to a donor fluorophore and an acceptor fluorophore, such as two different fluorescence protein domains (e.g., ECFP and EYFP). The two fluorophores are disposed so that, when the protein is folded, they are in close proximity to allow resonance energy transfer between them. The cells are bacterial, yeast, insect, plant, or mammalian cells, or, preferably, insect cells.

The just-described method includes determining the efficacy of the compound for treating the disease by monitoring cells emitting fluorescence from the donor or acceptor fluorophore upon irradiation of the donor fluorophore with an excitation light. In one embodiment, the determining step is conducted by identifying a percentage of cells emitting the fluorescence of the acceptor fluorophore. The compound is determined to be effective in treating the disease if the percentage of cells emitting fluorescence from the acceptor fluorophore is higher than that determined in the same manner on cells in a second medium, except that the second medium does not contain the compound. In another embodiment, the determining step is conducted by identifying a percentage of cells emitting the fluorescence of the donor fluorophore. The compound is determined to be effective in treating the disease if the percentage of cells emitting fluorescence from the donor fluorophore is lower than that determined in the same manner on cells in a second medium, except that the second medium does not contain the compound. In yet another embodiment, the determining step is conducted by identifying a resonance energy transfer efficiency of the cells. The compound is determined to be effective in treating the disease if the resonance energy transfer efficiency is higher than that determined in the same manner on cells in a second medium, except that the second medium does not contain the compound. The resonance energy transfer efficiency is derived using the following formula:

$$\text{Resonance energy transfer efficiency} = 1 - \frac{I_b}{I_a}$$

One can obtain the intensities of the donor fluorophore in presence and absence of the energy transfer (Ia and Ib), respectively, according to the method described in the Example below or other methods known in the art.

In a further aspect, the invention features a method of detecting a cell-lysis activity of a sample. The method includes (1) incubating in a first medium a sample and a plurality of cells that have a protein containing a fluorophore, e.g., ECFP, EGFP, EYFP, or DsRed; and (2) determining a percentage of cells emitting fluorescence upon irradiation of the fluorophore with an excitation light. The sample is determined to have a cell-lysis activity if the percentage of cells emitting fluorescence is lower than that determined in the same manner on cells in a second medium, except that the second medium does not contain the sample.

The invention features another method for detecting a cell-lysis activity of a sample. The method requires the use of a plurality of cells that have a protein containing a donor fluorophore and an acceptor fluorophore, such as two different fluorescence protein domains (e.g., ECFP and EYFP). The two fluorophores are disposed so that, when the protein is folded, they are in close proximity to allow resonance energy transfer between them. The method includes (1) incubating in a first medium a sample and the cells; (2) determining the cell-lysis activity of the sample by monitoring cells emitting fluorescence from the donor or acceptor fluorophore upon irradiation of the donor fluorophore with an excitation light. In one embodiment, the determining step is conducted by identifying a percentage of cells emitting the fluorescence of the acceptor fluorophore. The sample is determined to have a cell-lysis activity if the percentage of cells emitting fluorescence from the acceptor fluorophore is lower than that determined in the same manner on cells in a second medium, except that the second medium does not contain the sample. In another embodiment, the determining step is conducted by identifying a percentage of cells emitting the fluorescence of the donor fluorophore. The sample is determined to have a cell-lysis activity if the percentage of cells emitting fluorescence from the donor fluorophore is higher than that determined in the same manner on cells in a second medium, except that the second medium does not contain the sample. In yet another embodiment, the determining step is conducted by identifying a resonance energy transfer efficiency of the cells. The sample is determined to have a cell-lysis activity if the resonance energy transfer efficiency is lower than that determined in the same manner on cells in a second medium, except that the second medium does not contain the sample.

In both cell-lysis detecting methods, the cells are bacterial, yeast, insect, plant, or mammalian cells, or preferably, insect cells. They can be used to screen for agents, e.g., compounds or microorganisms, that kill unwanted cells, such as infectious bacterial cells, yeast cells, fungus cells, or cancerous cells.

The details of one or more embodiments of the invention are set forth in the description below. Other features, objects, and advantages of the invention will be apparent from the description and drawings, and from the claims.

DETAILED DESCRIPTION

The present invention relates to a non-lytic baculovirus. Host cells infected with it do not lyse. An expression system based on this non-lytic baculovirus has several advantages over conventional systems.

First, the engineered protein expressed in the host cells does not leak out of the host cells. Second, the host cell lysosomes do not break down to release proteases and, as a result, one can harvest the engineered protein without using expensive protease inhibitors. Finally, as endoplasmic reticules and Golgi bodies in the host cells remain intact and efficiently modify and transport engineered protein, this system is useful for producing glycoprotein, membrane protein, or secretory protein.

To produce an engineered protein, one can simply infect a host cell with a baculovirus of this invention, which contains an exogenous nucleic acid sequence encoding the protein using standard techniques. See, e.g., Pfeifer et al., 1997, Gene 188:183-190; and Clem et al., 1994, J Virol 68:6759-6762. Suitable host cells may vary depending on the designs of systems or consideration of specificity. Examples of suitable host cells include, but are not limited to, the cells derived from species ranging from insects to vertebrates. Preferred host cells are insect-derived cells and mammalian cells. Examples of the insect-derived cells include S2 cells, Kc cells, and C6/36 cells. Suitable mammalian cells include primary cells or cell lines from murine, rat, rabbit, porcine, or human sources. The expressed protein can be therapeutic protein. They can be used to express in a subject (e.g., a mammal, such as a human) a nucleic acid sequence encoding a protein that corrects a deficiency in gene expression. Examples of the proteins include vaccines, antibodies, biologically active peptides, cytokine and their receptors, growth factors and their receptors, and enzymes.

The baculoviruses of this invention can be used in detecting the folding of a protein of interest. Conventional analysis of protein folding is based on in vitro spectroscopic and thermodynamic methods (Garcia-Mira et. al., Science 298, 2191-2195). These in vitro methods require laborious protein purification, during which the proteins tend to be unfolded or degraded. An in vivo system is expected to allow one to better study protein folding. The baculoviruses of this invention provide such an in vivo system. More specifically, one can (1) design a fusion protein containing the protein of interest and a pair of donor and acceptor fluorophores, (2) express the fusion protein in a host cell, and (3) study the folding of the protein of interest by examining the fluorescence resonance energy transfer (FRET) between the two fluorophores.

The efficiency of FRET can be derived from the formula descried above. It is determined by the angular orientation and the distance between the donor and acceptor fluorophores. Typically, FRET takes places over a distance less than 100 Å, which is comparable to the dimension of most folded proteins. Thus, it allows one to study the folding status of a protein. Take the ECFP/EYFP pair for example, their Förster distance R0 (a distance at which the FRET efficiency is 50%) is 49 Å. FRET between them remains detectable over a distance of 78 Å (Bastiaens and Jovin 1996, Proc Natl. Acad. Sci. 93, 8407-8412; Bastiaens and Harpur 2001, Molecular Cloning—A laboratory manual, 3rd. Ed. Sambrook, J. and Russell, D. W. ed., A 18.69).

To detect the folding status of a protein, a donor fluorophore and an acceptor fluorophore are fused to or inserted into the protein so that (1) when the protein is unfolded/denatured, the two fluorophores are too far away to allow FRET, and (2) when it is folded and becomes more compact, the two fluorophores are brought closer enough for FRET to take place. The FRET can be detected by measuring the fluorescence emission of either the acceptor or the donor fluorophore according to the method described in the actual examples below or by other techniques known in the art. When a protein's N- and C-termini are in the same direction, the two fluorophores can simply be fused to the two termini, respectively. Indeed, many proteins have N- and C-termini in the same direction (see, e.g., Zhao, et al., 2001, J. Biol. Chem. 276, 12120-12127; Riedl, et al., 2001, Proc. Natl. Aced. Sci. USA 98, 14790-14795; and Cierpicki and Otlewski, 2002, J. Mol. Biol. 321, 647-658.). Otherwise, one can determine the positions to insert the two fluorophores based on the 3-D structural data of a protein, which can be obtained using techniques well known in the art, such as NMR and X-ray crystallography. See, e.g., Conti et al., 1996, Structure 4, 287-298.

The just-described detecting method can be used in real time to monitor the folding-denature status of a protein in response to various genetic changes (e.g., point mutation and presence of chaperone protein) or environmental changes (e.g., pH, temperature, and presence of certain compounds). Accordingly, it can be used to screening for conditions or compounds that enhance the folding of a protein of interest.

It is known that some genetic mutations compromise normal protein folding and lead to unfolded or misfolded protein. These proteins contribute to various disorders, ranging from cystic fibrosis to neurodegenerative diseases. See, e.g., Massiah et al., 1999, Biochemistry 38, 7453-7461; Travers, et al., 2000, Cell 101, 249-258; and Sherman and Goldburg, 2001, Neuron 29:15-32. Thus, compounds that facilitate protein folding can be used in treating such diseases.

To identify such compounds, one can use the above-described fusion protein that contains a donor fluorophore and acceptor fluorophore or cells (e.g., bacterial, yeast, insect, plant, or mammalian cells) containing such fusion protein. In one example, the cells are incubated in a first medium containing a test compound and a second medium free of the compound, respectively. One then (1) monitors in both media the cells emitting fluorescence from the donor fluorophore upon irradiation of the donor fluorophore with an excitation light and (2) identifies a percentage of cells emitting the fluorescence of the donor fluorophore. The compound is determined to be effective in treating a disease associated with misfolded protein if the percentage of cells emitting fluorescence from the donor fluorophore in the first medium is lower than that determined in the same manner on the cells in the second medium. Alternatively, one can identify a percentage of cells emitting the fluorescence of the acceptor fluorophore or the FRET efficiency on the cells in both media. The compound is determined to be effective in treating the disease if the percentage or FRET efficiency determined on the cells in the first medium is higher than that determined in the same manner on the cells in the second medium.

Compounds to be screened can be obtained using any of the numerous approaches in combinatorial library methods known in the art. Such libraries include: peptide libraries, peptoid libraries (libraries of molecules having the functionalities of peptides, but with a novel, non-peptide backbone that is resistant to enzymatic degradation), spatially addressable parallel solid phase or solution phase libraries, synthetic libraries obtained by deconvolution or affinity chromatography selection, the "one-bead one-compound" libraries, and antibody libraries. See, e.g., Zuckermann et al. (1994) J. Med. Chem. 37, 2678-85; Lam (1997) Anticancer Drug Des. 12, 145; Lam et al. (1991) Nature 354, 82; Houghten et al. (1991) Nature 354, 84; and Songyang et al. (1993) Cell 72, 767. Examples of methods for the synthesis of molecular libraries can be found in the art, for example, in: DeWitt et al. (1993) Proc. Natl. Acad. Sci. USA 90, 6909; Erb et al. (1994) Proc. Natl. Acad. Sci. USA 91, 11422; Zuckermann et al. (1994) J. Med. Chem. 37, 2678; Cho et al. (1993) Science 261, 1303; Carrell et al. (1994) Angew. Chem. Int. Ed. Engl. 33, 2059; Carell et al. (1994) Angew. Chem. Int. Ed. Engl. 33, 2061; and Gallop et al. (1994) J. Med. Chem. 37,1233. Libraries of compounds may be presented in solution (e.g., Houghten (1992) Biotechniques 13, 412-421), or on beads (Lam (1991) Nature 354, 82-84), chips (Fodor (1993) Nature 364, 555-556), bacteria (U.S. Pat. No. 5,223,409), spores (U.S. Pat. No. 5,223,409), plasmids (Cull et al. (1992) Proc. Natl. Acad. Sci. USA 89, 1865-1869), or phages (Scott and Smith (1990) Science 249, 386-390; Devlin (1990) Science 249, 404-406; Cwirla et al. (1990) Proc. Natl. Acad. Sci. USA 87, 6378-6382; Felici (1991) J. Mol. Biol. 222, 301-310; and U.S. Pat. No. 5,223,409).

This invention also features a method for detecting a cell-lysis activity of a sample. This method can be used to screen for cell lysis agents. To practice this method, one needs cells expressing a protein containing at least one fluorophore. One can use bacterial, yeast, fungal, insect, plant, or mammalian cells. The agents thus identified can be used to kill unwanted cells, such as infectious bacterial cells, yeast cells, fungus cells, or cancerous cells.

In one embodiment, cells expressing a protein containing one fluorophore are used. Two groups identical cells are incubated in a first medium containing a test sample and in a second medium free of the sample, respectively. Upon irradiation of the fluorophore with an excitation light, cells emitting fluorescence from the fluorophore are monitored to determine the percentage of the cells emitting the fluorescence. The sample is determined to have a cell-lysis activity if the percentage determined on the cells in the first medium is lower than that determined in the same manner on the cells in the second medium.

In other embodiments, one uses cells expressing a fusion protein containing a donor fluorophore and an acceptor fluorophore. He can respectively incubate the cells in a first medium containing a test sample and in a second medium free of the sample. Upon irradiation of the donor fluorophore with an excitation light, he monitors in both media cells emitting fluorescence from the donor fluorophore to identify a percentage of cells emitting the fluorescence of the donor fluorophore. The sample is determined to have a cell-lysis activity if the percentage is higher than that determined in the same manner on the cells in the second medium. Alternatively, he can identify a percentage of cells emitting the fluorescence of the acceptor fluorophore or the FRET efficiency on the cells in both media. The sample is determined to have a cell-lysis activity if the percentage or FRET efficiency determined on the cells in the first medium is lower than that determined in the same manner on the cells in the second medium.

The examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Cells and Viruses

The *Spodoptera frugiperda* IPLB-Sf21 (Sf21) cell line was cultured in a TNM-FH insect medium containing 8% heat-inactivated fetal bovine serum (Lee et al., 1998, J. Virol. 72, 9157-9165 and Lin et al., 1999, J. Virol. 73, 128-139). It was used for the propagation and infection of wild type and recombinant baculoviruses. All viral stocks were prepared and titers were determined according to the standard protocol described by O'Reilly et al., 1994, Baculovirus Expression Vectors: A Laboratory Manual, Oxford University Press, New York.

Construction of Plasmids and Viruses

Plasmid pAB$^h$cmEpL, which contains two promoters to drive the expression of two different foreign proteins, was constructed as follows. The coding sequence of EGFP, derived from pEGFP-1 (Clontech, Palo Alto, Calif.), was inserted into a pBacPAK8 transfer vector (Clontech). The EGFP coding sequence was under the control of a CMV minimal promote, which was enhanced by an hr 1 sequence (Lo et al., 2002, J. Biol. Chem. 277:5256-5264.). Another DNA sequence encoding firefly luciferase (LUC) was inserted into the same transfer vector and was under the control of polyhedrin promoter. The resultant plasmid, pAB-$^h$cmEpL, was co-transfected with vAcRP23.Laz (PharMingen, San Diego, Calif.), a linearized viral DNA of AcMNPV, into Sf21 cells using Lipofectin (Invitrogen, Carlsbad, USA) to produce recombinant virus vAB$^h$cmEpL.

To generate a concatenated fusion gene, eyfp-luc-ecfp, a DNA fragment encoding LUC was prepared using PCR from a pTRE-Luc vector (Clontech) with primer pairs: forward primer, 5'-GAAGATCTTTGGTCCCTCGTG-GAAGCATGGAAGACGCCAAAAACATA-3'(SEQ ID NO:1) and reverse primer, 5,'-CACCGGTCCATGATGAT-GATGATGATGCAATTCCACTTTCCGCCCTT-3'(SEQ ID NO:2). The forward primer was designed to contain a Bgl II site (underlined) and a thrombin cutting sequence (bold) just upstream of the initiation codon. The reverse primer had an Age I site (underlined) downstream of the hexa-histidine tag (italics). After PCR amplification, the products were ligated into a pCR-Blunt II-TOPO vector (Invitrogen), to generate an intermediate plasmid. This intermediate plasmid, pBTII-Luc, was digested by Bgl II and Age I, and the released fragment was inserted into a pECFP-N1 vector (Clontech), to generate a plasmid containing the luc-ecfp fusion sequence. The resultant plasmid, pcLC, was used as a template to amplify the luc-ecfp fusion gene by PCR with the forward primers just described and another reverse primer, 5'-GGGGTACCAATATTAACGCTTAC-3'(SEQ ID NO:3) (Kpn I site underlined). The PCR products were inserted into a pCR-Blunt II-TOPO vector to prepare another intermediate plasmid containing luc-ecfp fusion gene, from which a Bgl II and Kpn I-digested fragment was cloned into the Bgl II-Kpn I site of a pEYFP-C 1 vector (Clontech). The resultant plasmid, pcYLC, contained the eyfp-luc-ecfp tandem fusion gene that was driven by an hr1 sequence-enhanced minimal CMV promoter. The fusion gene encoded a fusion protein EYFP-LUC-ECFP (YLC), in which LUC was sandwiched between a N-terminally tagged EYFP and a C-terminally tagged ECFP.

The just-described pcYLC was cut by Nhe I and Not I to release a fragment containing the eyfp-luc-ecfp coding sequence. This fragment was then cloned into the Xba I-Not I site of a pBacPAK8 vector. The resultant transfer plasmid, pABpYLC, contained the eyfp-luc-ecfp coding sequence under the control of the polyhedrin promoter. The polyhedrin promoter of pABpYLC was then replaced with the above-described hr1 sequence-enhanced minimal CMV promoter to make a pAB$^h$cmYLC transfer vector.

Two additional transfer plasmids, pABpC and pABpY, were created by cutting pECFP-N1 with Pst I and Not I and digesting pEYFP-C1 with Nhe I and Kpn I, and ligating the fragments into the Pst I/Not I and Xba I/Kpn I sites of pBacPAK8 vectors, respectively. pABpLC was prepared by the removal of eyfp from pABpYLC with Bgl II and BamH I digestion. It contained the luc-ecfp fusion gene Recombinant baculoviruses were prepared by co-transfection 0.1 µg of various transfer plasmids described above (pABpYLC, pAB$^h$cmYLC, pABpLC, pABpC, and pABpY, respectively) and 0.1 µg of linearized AcMNPV viral DNA (BaculoGold, Pharmagen, San Diego, Calif.) into cells using Lipofectin. The resultant recombinant baculoviruses were named as vABpYLC, vAB$^h$cmYLC, vABpLC, vABpC, and vABpY, respectively.

Mutagenesis and Isolation of Nonlytic Baculovirus Mutants

General and saturated mutagenesis of the genome of Autographa californica nucleopolyhedrovirus (AcMNPV) was conducted to generate mutants. The mutants were then used to infect host cells. Since host cells infected with nonlytic and lytic baculovirus viruses are morphologically indistinguishable before cell lysis, it is difficult to isolate nonlytic mutants at the early phrase after infection. On the other hand, after cell lysis can be appreciated by standard cytology techniques, too many virus particles are already in the medium and are difficult to isolate pure virus clones. GFP in a host cell freely leaks out before cell lysis can be appreciated, it therefore was used as an indicator for identifying and isolating nonlytic viruses.

Sf21 cells ($2\times10^5$) were infected with vAB$^h$cmEpL at a multiplicity of infection (moi) of 1 TCID50 per cell and incubated at 26 or 33° C. in the presence of 5-bromodeoxyuridine (BrdU) at concentrations of 10, 30, and 40 µg/ml. The culture media were harvested at 5 days post-infection (dpi), and excess BrdU was removed by dialysis in a buffer (137 mM NaCl, 29 mM KCl, 4.3 mM $Na_2HPO_4\cdot7H_2O$, 1.4 mM $KH_2PO_4$, pH 7.2, plus 0.5% w/v BSA). Mutant virus were purified by end-point dilution for three rounds on 96-well plates, and the purified viruses were used to infect individual wells of 96-well plates. 25 µl medium from each well was removed and used to infect Sf21 cells. The infected cells were incubated at 26° C. At 5 and 8 dpi, the expression of EGFP was examined using a fluorocytometer to identify viral isolates that caused high cellular EGFP levels.

11,603 clones were isolated. It is known that the baculovirus genome has less than 154 genes/open reading frames. These 11,603 clones should be more than enough to cover all the possible viral genes, the mutations of which would result in nonlytic infection. Among them, 118 mutant clones showed reduction in cell lyses as indicated by the retention of EGFP in cells. In these 118 clones, 20 clones, i.e., A1, A2, A3, C4, 1028, 1044, 1053, 1071, 1081, 1085, 1091, 1094, 3058, 3074, PN8, PN9, PN19, PN23, PN24, and PN121, were further analyzed. Clones 1081 and C4 were deposited, on Dec. 13, 2006, at the China Center for Type Culture Collection, Wuhan, Hubei, 430072, China, where they were given Accession Numbers CCTCC V200610 and CCTCC V200611. respectively.

These viruses were different from the p35 mutant disclosed in Lee et al., 1998, Journal of Virology 72, 9157-9165, as all had intact p35 gene. Further, after infection by a p35 mutant, most host cells (about 95-99%) were lyzed. In contrast, after infection with one of the 21 mutants, the majority of host cells remain intact. The cell lysis caused by these mutants was significantly less than that by the vAB-hcmEpL virus. The results were even more significant if higher moi was used. Also, it was found that significant more EGFP proteins were produced by all these mutants than by vABhcmEpL. As CMVm promoter drove the expression of EGFP, the results suggest that CMVm promoter is more active in cells infected with the mutants.

Each of the viruses described above had a LUC-encoding sequence under the control of the polyhedrin promoter, a very late promoter. To study the activity of this promoter, the activity of luciferase was examined. More specifically, cells infected with each virus were lysed for 25 min in 100 µl of a cell lysis reagent containing 100 mM potassium (pH 7.8), 1 mM EDTA, 10% glycerol, 1% Triton X-10, and 7 mM β-mercaptoethanol. After centrifugation at 14,000 rpm for 10 min, the supernatant or lysate (50 µl) was collected and mixed with 180 µl of LUC assay reagent containing 25 mM Tricine (pH 7.8), 15 mM potassium phosphate (pH 7.8), 15 mM MgSO$_4$, 4 mM EGTA, 1 mM ATP, and 0.1 mM dithiothretitol. Fifty microliters of a luciferin (Promega, Madison, Wis.) solution was added into with the mixture, and relative light units were measured using a luminometer (Berthold, Lumat LB 9501, Bad Wildbad, Germany). The total protein concentration of the cell lysate was determined using a Coomassie protein assay reagent (Pierce, Lselin, USA). Higher activities of the polyhedrin promoter were found in host cells infected with clones 1081, 3058, PN8, PN9, PN19, PN23, PN24 and PN121.

Among the above-described 21 mutants, clone C4 leaded to the least cell lysis and PN24 had the strongest polyhedrin promoter activity. Both were further examined.

To generate nonlytic C4 recombinant viruses encoding an engineered protein YLC, pABpYLC and pAB$^h$cmYLC were transfected into Sf21 cells. The cells were then infected with the C4 nonlytic baculovirus to generate recombinant viruses vC4pYLC and vC4$^h$cmYLC. In these baculoviruses, the sequences encoding YLC were under the controls of polyhedrin promoter and a synthetic early promoter, respectively. All recombinant viruses were purified by three rounds of end-point dilution.

These recombinant nonlytic C4 baculoviruses and the lytic parental vABhcmEpL virus were used to infect Sf21 cells at 1 moi, respectively. At 5 dpi., the cells were examined by fluorescence microscopy. It was found that less than 40% of cells infected with vABhcmEpL contained EGFP protein. In contrast, more than 95% of cells infected with C4 baculoviruses contained EGFP. The result again indicates that the EGFP could be used to detect cell lysis before cell lysis can be appreciated by standard microscopic techniques. It also indicates that conventional baculoviruses lead to leak of engineered protein upon cell lysis and lower protein yields.

Cells infected with the lytic and nonlytic baculoviruses were further examined by electron microscopy. It was found that nonlytic C4 virus-infected cells had intact cytoplasmic membrane and ER. In contrast, those infected with the lytic parental virus vABhcmEpL had severe damages in these organelles. ER is an important organelle for protein modification, folding, sorting, and trafficking (Stevens and Argon, 1999, Seminars in Cell and Developmental Biology 10, 443-454.). Damaged ER leads to poor quality of engineered protein. The above results indicate that nonlytic C4 baculovirus-infected cells produce better folded engineered protein than those infected with lytic baculovirus. In addition, folding of engineered protein requires cellular chaperone proteins. As these proteins may leak out from lytically-infected cells but not from non-lytically infected ones, the engineered protein is better folded in the nonlytic baculovirus-host cell system.

In Vitro Protein Folding

FRET technology was used to examine the folding of luciferase (LUC), which contains 521 residues and has a molecular weight of 62 kD. In a folded LUC, the distance between its N- and C-terminus is about 40 Å (Conti et al., 1996, Structure 4, 287-298). If its N and C-termini are fused to EYFP and ECFP, respectively, the distance between the centers of the two fluorescent proteins was estimated to be 40-60 Å. Assuming that the mutual orientation of the two fluorophores was random and freely tumbling, only a limited FRET. Hence, only tightly folded luciferase could allow FRET between the two fluorophores.

The above-described YLC-encoding vectors were used to generate 4 recombinant viruses: 2 conventional lytic vABpYLC and vAB$^h$cmYLC, and 2 nonlytic vC4pYLC and vC4$^h$cmYLC. YLC fusion protein was generated in host cells infected with these baculoviruses using standards techniques and purified using a HisBind Kit (Novagen, Wis., USA) and Sephacryl S-200 (Pharmacia, Uppsala, Sweden) gel filtration resins. Its purity was checked by SDS-PAGE, and the concentration was determined using a Micro BCA Kit (Pierce).

The fluorescence emission spectra of the YLC pro BOWMAN Series 2, Spectronics Unicam, Rochester, USA). The excitation wavelength was set at 436 nm, and the emission spectrum from 450 to 600 nm was recorded. For comparison, the fluorescence emission of the LUC-ECFP fusion protein (LC) and EYFP were measured after these proteins were excited by lights of 436 and 510 nm, respectively. All spectra data were corrected for background fluorescence from the buffers. The emission spectrum showed a peak at 475 nm (cyan emission from ECFP) and, more importantly, an obvious emission peaked at 530 nm (yellow emission from EYFP). If LUC is properly folded, ECFP (the donor) and EYFP (the acceptor) are in close proximity to allow FRET between them, producing yellow fluorescence emission. Otherwise, no yellow emission is detected. These results indicate that FRET took place in the fusion protein, which was unexpected given the size of LUC (521 residues), the estimated distance between the centers of the two fluorescent proteins (40-60 Å), and the R0 value for ECFP/EYFP pair (49 Å).

To test the specificity of the FRET, the YLC fusion protein was engineered to contain a thrombin digestion site between EYFP and the rest of the fusion protein. After the EYFP domain was removed from the rest of the YLC protein by a thrombin treatment, the yellow fluorescence was abolished. This result indicates that the FRET is specific.

Further, the YLC fusion protein was incubated with urea (from 0 M to 5 M) and monitored for its fluorescence. It was found that, as urea concentration increased, the intensity of the 475-nm fluorescence emission increased, while that of the 530-nm emission decreased and returned to the background level in the presence of 5 M urea. It is known that fluorescent proteins, including ECFP and EYFP, are resistant to urea (Ward, 1998, Green Fluorescence Protein—Properties, application, and Protocols, Chalfie, M. and Kain, S. ed., pp45-75. New York: Wiley-Liss). In contrast, many other proteins, such as LUC, are not and denature in presence of low concentration of urea (~1 M) or guanidinium chloride (Herbst et al., 1997, J. Biol. Chem. 272, 7099-7105). Thus, these results indicate that the change in the yellow emission from EYFP is a function of the folding/denaturing status of LUC.

In Vivo Protein Folding

The just-described nonlytic baculovirus-host cell system and FRET technology were used to examine folding of luciferase in Sf21 insect cells.

Sf21 cells were infected with various recombinant baculoviruses (vABpYLC, vABhcmYLC, vC4pYLC, and vC4hcmYLC) expressing engineered fusion YLC proteins. They were then examined by laser scanning confocal fluorescence microscopy (Pascal LSM, Zeiss, Oberkochen, Germany), and pictures were taken using a ×40 objective len. The cells were then excited by a laser of 458 nm provided by an argon laser. Fluorescence emission was separated as cyan channel (from 475 nm to 515 nm and yellow channel (>530 nm). For discrimination, blue and yellow pseudocolor was assigned to the cyan and yellow channels, respectively. For cells emitting similar intensities of both cyan and yellow fluorescence emissions, a combination of the two pseudocolors (pale-yellow or white) was assigned. For ECFP detection, fluorescence emission was collected through a dual-wavelength beamsplitter at 458/514 nm and a longpass emission filter at 475 nm. For EYFP detection, the same beam splitter and a long pass emission filter at 530 nm were used. For simultaneous detection of cyan and yellow fluorescences, the infected cells were excited by a laser of 458 nm. The acceptor yellow fluorescence was collected using the 458/514-nm beam splitter and a long pass 530-nm emission filter, whereas the donor cyan fluorescence emission was separated by locating another 515-nm beam splitter and a band pass 475-525 nm emission filter after the 458/514-nm beam splitter.

It was found that lytic baculovirus-infected cells showed either blue or yellow with some white emission. On the contrary, nonlytic baculovirus-infected cells were mostly pale-yellow to white.

To determine the efficiency of the FRET of each baculovirus-host cell system, photobleaching experiment was conducted. Sf21 cells were infected with vABpYLC, vAB$^h$cmYLC, vC4pYLC, and vC4$^h$cmYLC in the same manner as described above. Selected infected cells were excited by a light of 458 nm. The intensities of cyan fluorescence (Ib) and yellow fluorescence emissions were measured. Afterwards, each cell was photobleached by an argon laser of 514 nm (excitation light for EYFP) to saturate the EYFP. As a result, cyan fluorescence from the infected cell was dequenched or recovered due to blockage of the FRET. Then, the intensity of cyan fluorescence (Ia) was measured. The FRET efficiency was then calculated using the following formula:

$$\text{FRET efficiency} = 1 - \frac{I_b}{I_a}.$$

The efficiency reflects the fraction of cyan fluorescence emission energy that is transferred to the yellow fluorescence protein.

It was found that the FRET efficiencies in vABpYLC-, vAB$^h$cmYLC-, vC4pYLC-, and vC4$^h$cmYLC-host cell systems were 0.08±0.08, 0.12±0.1, 0.21±0.08, and 0.23±0.09, respectively. The difference between early and very late promoter lytic systems was less significant ($0.05<p<0.1$). In contrast, the difference between the lytic and nonlytic systems was statistically significant ($p<0.05$). These results indicate that YLC protein in the lytic baculovirus-host cell system is degraded. The loss of one or both of ECFP and EYFP domains, or the linkage between them lead to a lower FRET efficiency. Accordingly, FRET efficiency, as well as the donor or acceptor fluorescence emission, reflects cell or protein lysis status, in addition to protein folding. The results also indicate that the nonlytic system described herein is superior to the conventional system for studying protein folding.

Theoretically, cells emitting a cyan fluorescence have low FRET efficiencies. In contrast, those emitting pale-yellow or white cells should have satisfactory FRET efficiencies. In particular, cells emitting yellow fluorescence should have the highest efficiencies, as all cyan fluorescence energy is transferred to EYFP. Some ABpYLC or vABhcmYLC-infected cells emitted yellow fluorescence. However, after photobleaching, they showed no fluorescence let alone enhanced cyan fluorescence, indicating no FRET. This discovery indicates that that infection of lytic vABpYLC or vABhcmYLC generated much of YLC fragments, instead of full length YLC. As a result, no FRET took place. Thus, the convention baculovirus system is inferior to the non-lytic system described herein for FRET analysis.

It has been reported that the FRET between EGFP and EYFP has low efficiencies of 0.10-0.15 (Harpur et al., Nature Biotechnol. 19, 167-169). Given the R0 value of ECFP/EYFP pair (4.9 nm) and the size of LUC, it was unexpected that the YLC fusion protein described above had a high FRET efficiency (>0.15). It is possible that this high FRET efficiency results from a favorable orientation of fluorophore transition dipoles due to the proper and flexible linker molecule or from a large amount of EYFP due to the high protein yield of the baculovirus expression system.

Alternatively, the higher efficiency may be an overestimation of the dimerization of fluorescence proteins (Zacharias et al., 2002, Science 296, 913-916.). Such dimerization or overcrowding might lead to inter-molecule energy transfer and in turn a high FRET efficiency. To examine whether this is the case, Sf21 cells were co-infected with two recombinant baculoviruses bearing ecfp and eyfp genes at an moi of 10 (to ensure coinfection of the same cells), and examined in the same manner described above. It was found that only limited FRET efficiency (3%-8%) was achieved, suggesting that inter-molecule energy transfer does not lead to high FRET efficiencies. Further, after adjusting for this basal efficiency, the above described FRET efficiencies of vABpYLC-, vABhcmYLC-, vC4pYLC-, and vC4hcmYLC-host cell systems (i.e., 0.08, 0.12, 0.21, and 0.23), were 0.00-0.05, 0.04-0.09, 0.13-0.18, and 0.15-0.20, respectively. The adjusted efficiencies for the lytic and nonlytic system were even more statistically significant.

Proteins Expression

After infecting with wild type baculoviruses, host cells are eventually lysed at the very late phase of viral infection, a time close to activation of the polyhedrin promoter and the expression of a large amount of engineered protein. It is known that cellular machinery such as foldase and chaperones is necessary for the proper folding of engineered proteins. Without proper assistance with folding, they tend to aggregate (Herbst et al., 1997, J. Biol. Chem. 272, 7099-7105.). It is also known that unfolded proteins are usually subject to degradation (Sherman and Goldburg, 2001, Neuron 29:15-32.). This may cause the low FRET efficiencies in lytically infected cells described above. To test this hypothesis, western blot analysis was conducted to evaluate the YLC proteins produced from the above-described four expression systems.

Protein samples were separated on a 10% SDS-PAGE, and then electrotransferred onto a PVDF membrane. The membrane was blocked in Tris-buffered saline (TBS) containing 5% non-fat milk at room temperature for 4 h while being gently shaken on an orbital shaker. The membrane was then incubated with a first antibody specifically against LUC (1:2500, Sigma, St. Louis, Mo.) or GFP variants (1:1000; Clontech) in TBS containing 5% nonfat milk and 0.05% Tween-20 overnight at room temperature with constant shaking. Unbounded antibodies were removed by three 10-min washes in TBS containing 0.1% Tween-20 (TTBS). The membrane was incubated with a secondary antibody, a 1:2500-diluted horseradish peroxidase-conjugated anti-rabbit IgG (Goat) (PerkinElmer, Wellesley, USA), for 1 h at room temperature. After four 15-min washes with TTBS, protein bands bounded by antibodies were visualized by chemical luminescence (Western Lightning, PerkinElmer) and developed on Kodak film (Pharmacia).

It was shown that full-length YLC (ca. 110 kD) was only found in cells infected with the nonlytic viruses vC4pYLC or vC4hcmYLC. In contrast, serious protein degradation was found in cells infected with the lytic viruses vABpYLC and vABhcmYLC. As to blotting using anti-GFP protein, a major band at 27 kD was found in cells infected with vABpYLC, and well matched EYFP or ECFP made using the viruses vABpY and vABpC, indicating that the 110 kD YLC fusion protein was degraded. These results indicate that engineered protein expressed from cells infected with the nonlytic baculovirus has better quality than that from cells infected with and conventional lytic baculovirus Expression of Membrane Protein An engineered membrane protein, CHL1-DsRed, was expressed using the above-described nonlytic baculoviruses, as well as wild type baculoviruses. CHL1, an *Arabidopsis thaliana* membrane protein, is a nitrate/chlorate transporter and a member of the proton-dependent oligopeptide transporter (POT) family. It has 12 transmembrane alpha-helical and a cytosolic N-terminal domain (Tsai et al. 1993, Cell 72(5): 705-13).

A DNA sequence encoding the first 131 amino acid residues of CHL1 protein was synthesized according to the baculovirus genetic codes (Ranjan and Hasnain, 1995, Indian J. Biochem. Biophys. 32(6): 424-8; Levin and Whittome, 2000, J. Gen. Virol. 81(Pt 9): 2313-25). This sequence, encoding 3 transmembrane alpha helixes, was engineered to contain a Kozak consensus sequence to facilitate gene translation. In addition, its second peptide was mutated from serine (TCC) to glycine (GGC), and 8 nucleotides CCTC-CACC was added 5' end to the ATG codon. This DNA sequence was then cloned into a pDsRed vector (Clontech) and in-frame linked to the DsRed gene, which encoded a red fluorescent protein. The resultant chl1-DsRed fusion gene was amplified by PCR with a BamHI site-containing 5'-primer and a Not I site-containing 3'-primer. The product was subcloned into a pBakPAK8 vector to generate the vector pABpCR. The CHL1-DsRed fusion gene was also amplified by PCR with an Nhe I-site-containing 5'-primer and a Bcl I-site-containing 3'-primer, and subcloned into the pAB$^h$cmEpL vector described above to generate the vector pAB$^h$cmCR. In both vector, the fusion gene was under the control of the hr enhanced CMV minimal promoter. The DNA sequence of an hsp70 (heat shock) promoter was cloned to the Sac II site of pDsRed. The fragment containing this hsp70 promoter and the DsRed gene was then subcloned into EcoRV site of the pBacPAK8 vector to generate pAB-hRpX.

The hydropathy plot of the CHL1-DsRed protein was generated using Kyte & D oolittle's method (Kyte and Doolittle, 1982, J. Mol. Biol. 157(1): 105-32) and the Expert Protein Analysis System (ExPASy) (Gasteiger et al., 2003, Nucleic. Acids Res. 31(13): 3784-8.). Three hydrophobic domains in the N-terminus region were distinguishable. The C-terminal DsRed domain exhibited much lower hydrophobicity. It was predicted that this fusion protein, once expressed in a host cell, should be located in the plasma membrane via its N-terminal CHL1 domain, and its C-terminal DsRed domain protrudes from the plasma membrane.

The just-described pABpCR and pAB$^h$cmCR were cotransfected with genomic DNAs of vAB$^h$cmEpL, the above-described C4, and PN24 using standard techniques to generate vABpCR, vAB$^h$cmCR, C4-pCR, C4-$^h$cmCR, PN24-pCR, PN24-$^h$cmCR, respectively. Selected viral clones were then amplified, undergone genomic DNA extraction, and subjected to electrophoresis after HindIII digestion to confirm the quality of extracted DNA. Titered viral stocks were stored in screw sealed vials at 4° C.

Sf21 cells were infected with the recombinant viruses just described. Their fluorescence levels were measured on 1 to 8 dpi. The measuring was repeated 3 times each day and 3 duplicates were made in each. Nine sets of data were obtained, calculated, and plotted. It was found that cells infected with vC4$^h$cmCR had the highest fluorescence level. Also, those infected with vC4 pCR had higher level than those infected with vPN24 pCR, vAB$^h$cmCR, or vABpCR.

The 3D models reconstructed from the confocal microscopy of Sf21 cells infected with the nonlytic baculovirus resembled hollow spheres covered by red clusters on their surfaces. In contrast, the cells infected with vABhRpX gave a 3D model resembling a solid ball. Cross-sections of these 3D models confirmed the differences between cells expressing membrane DsRed proteins and cytosolic DsRed proteins.

These results suggest that membrane protein is better processed and transported in the cells infected with non-lytic baculoviruses than in those with conventional lytic baculoviruses. This advantage may not due to a strong promoter, but to the intact intracellular organelles, such as the ER, Golgi complex, and lysosomes in the cells infected with non-lytic baculoviruses.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A recombinant baculovirus that infects host cells without lyzing the host cells, wherein the recombinant baculovirus contains an intact p35 gene, and the recombinant baculovirus is or 1081.

2. The recombinant baculovirus of claim 1, comprising an exogenous nucleic acid sequence nucleic acid sequence encoding a polypeptide.

3. A method of expressing a polypeptide in a host cell, comprising infecting the host cell with the recombinant baculovirus of claim 1, wherein the baculovirus further contains an exogenous nucleic acid sequence nucleic encoding the polypeptide.

4. The recombinant baculovirus of claim 2, wherein the polypeptide contains a fluorophore.

5. The recombinant baculovirus of claim 4, wherein the fluorophore is ECFP, EYFP, EGFP, or DsRed.

* * * * *

UNITED STATES PATENT AND TRADEMARK OFFICE
CERTIFICATE OF CORRECTION

| | |
|---|---|
| PATENT NO. | : 7,223,560 B2 |
| APPLICATION NO. | : 10/775050 |
| DATED | : May 29, 2007 |
| INVENTOR(S) | : Yu-Chan Chao |

Page 1 of 1

It is certified that error appears in the above-identified patent and that said Letters Patent is hereby corrected as shown below:

Col. 15, claim 1, line 4, add --C4-- after "is".

Signed and Sealed this

Eighteenth Day of September, 2007

JON W. DUDAS
*Director of the United States Patent and Trademark Office*